United States Patent
Feldmann et al.

(10) Patent No.: US 7,601,892 B2
(45) Date of Patent: Oct. 13, 2009

(54) NUCLEOTIDE SEQUENCES AND POLYPEPTIDES ENCODED THEREBY USEFUL FOR MODIFYING PLANT CHARACTERISTICS

(75) Inventors: Kenneth A. Feldmann, Newbury Park, CA (US); Greg Nadzan, Woodland Hills, CA (US); Noah Theiss, Woodland Hills, CA (US)

(73) Assignee: Ceres, Inc., Thousand Oaks, CA (US)

( * ) Notice: Subject to any disclaimer, the term of this patent is extended or adjusted under 35 U.S.C. 154(b) by 307 days.

(21) Appl. No.: 11/139,425

(22) Filed: May 27, 2005

(65) Prior Publication Data

US 2006/0010518 A1    Jan. 12, 2006

Related U.S. Application Data

(60) Provisional application No. 60/575,183, filed on May 27, 2004.

(51) Int. Cl.
*C12N 15/82* (2006.01)
*C12N 5/04* (2006.01)
*A01H 5/00* (2006.01)
*A01H 5/10* (2006.01)

(52) U.S. Cl. .................. 800/298; 800/278; 800/290; 800/287; 435/419

(58) Field of Classification Search .............. 536/23.1, 536/23.6; 435/320.1, 410, 419; 800/278, 800/298
See application file for complete search history.

(56) References Cited

U.S. PATENT DOCUMENTS

2004/0045049 A1    3/2004    Zhang et al.

FOREIGN PATENT DOCUMENTS

WO    WO-0198480    12/2001

OTHER PUBLICATIONS

Kano-Murakami et al (1993, FEBS 334:365-368).*
Bowie et al, Science 247:1306-1310, 1990.*
McConnell et al, Nature 411 (6838):709-713, 2001.*
Alexandrov et al (2000, EP1033405-A2, Geneseq Accession No. AAC46829).*
Koornneef, M et al., "A genetic and physiological analysis of late . . . ," Mol Gen Genet (1991) 229: 57-66: XP 002018289.
GenBank Database Accession No. Q8LFA6; Oct. 1, 2002; Brover, et al; XP002351002.
GenBank Database Accession No. AB022216; Jan. 15, 1999; Sato, et al; XP002351003.
GenBank Database Accession No. AX461381; Jul. 8, 2002; Budworth, et al; XP00235104.
EMBL-Bank Database Accession No. AAG41438; Oct. 18, 2000; Alexandrov, et al.; (*Arabadopsis thaliana* protein fragment SEQ ID No. 51557). XP002351005.
EMBL-Bank Database Accession No. AAG52927; Oct. 18, 2000; Kennedy, et al.; (*Arabadopsis thaliana* protein fragment SEQ ID No. 67332); XP002351006.
GenBank Database Accession No. Q7XPK3; Oct. 1, 2003; Feng, et al; XP002351007.
GenBank Database Accession No. Q6ZF15; Oct. 1, 2001; Sasaki, et al; XP002351008.
GenBank Database Accession No. AY084955; Jun. 14, 2002; Haas, et al; XP002351001.

* cited by examiner

*Primary Examiner*—Stuart F. Baum
(74) *Attorney, Agent, or Firm*—Birch, Stewart, Kolasch & Birch LLP

(57) ABSTRACT

Isolated polynucleotides and polypeptides encoded thereby are described, together with the use of those products for making transgenic plants with modified biomass.

21 Claims, No Drawings

NUCLEOTIDE SEQUENCES AND POLYPEPTIDES ENCODED THEREBY USEFUL FOR MODIFYING PLANT CHARACTERISTICS

This Nonprovisional application claims priority under 35 U.S.C. § 119(e) on U.S. Provisional Application No(s). 60/575,183 filed on May. 27, 2004, the entire contents of which are hereby incorporated by reference.

FIELD OF THE INVENTION

The present invention relates to isolated polynucleotides, polypeptides encoded thereby, and the use of those sequences for making transgenic plants with modified biomass.

BACKGROUND OF THE INVENTION

Plants are constantly exposed to a variety of biotic (i.e., pathogen infection and insect herbivory) and abiotic (i.e., high or low temperature, drought, and salinity) stresses. To survive these challenges, plants have developed elaborate mechanisms to perceive external signals and to manifest adaptive responses with proper physiological and morphological changes (Bohnert et al., 1995). It would, therefore, be of great interest and importance to be able to identify genes that confer increased or modified biomass to thereby enable one to create transformed plants (such as crop plants) with improved characteristics.

In the field of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. (Zhang et al. (2004) *Plant Physiol.* 135:615). There is a need for generally applicable processes that improve forest or agricultural plant growth potential. Therefore, the present invention relates to a process for increasing the abiotic stress tolerance and consequently the growth potential in plants, characterized by expression of recombinant DNA molecules stably integrated into the plant. genome. There is a need for generally applicable processes that improve forest or agricultural plant growth potential. Therefore, the present invention relates to a process for increasing biomass.

SUMMARY OF THE INVENTION

The present invention, therefore, relates to isolated polynucleotides, polypeptides encoded thereby, and the use of those sequences for making transgenic plants with modified biomass.

The present invention also relates to processes for improving the biomass characteristics in plants, recombinant nucleic acid molecules and polypeptides used for these processes and their uses, as well as to plants with an increased growth potential.

Unless otherwise defined, all technical and scientific terms used herein have the same meaning as commonly understood by one of ordinary skill in the art to which this invention belongs.

DETAILED DESCRIPTION OF THE INVENTION

1. Definitions

The following terms are utilized throughout this application:

Biomass: "Biomass," as referred to within, is the total amount or mass of a plant, part of a plant or product(s) of a plant. An increase in biomass is determined using a statistical analysis which shows that the experimental's biomass is greater than that of the control at a confidence level of 95%. Each plant species has the capability of producing a certain amount of biomass. It is not possible to generalize as to what would be an increase or decrease in biomass in absolute terms. Statistical approaches to measuring biomass and distinguishing plants that produce high or low biomass are well known in the art.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s).

Endogenous: The term "endogenous," within the context of the current invention refers to any polynucleotide, polypeptide or protein sequence which is a natural part of a cell or organisms regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al. *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical and within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily to the same degree. Typically, comparable proteins give the same characteristics where the quantitative measurement due to one of the comparables is at lest 20% of the other; more typically, between 30 to 40%; even more typically, between 50-60%; even more typically, 70 to 80%; even more typically between 90 to 100%.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter, which can be utilized with the polynucleotides of the present invention, is PARSK1, the promoter from the *Arabidopsis* gene encoding a serine-threonine kinase enzyme, and which promoter is induced by dehydration, abscissic acid and sodium chloride (Wang and Goodman, *Plant J.* 8:37 (1995)). Examples of environmental conditions that may affect transcription by inducible promoters include anaerobic conditions, elevated temperature, or the presence of light.

Masterpool: The "master pools" discussed in these experiments are a pool of seeds from five different transgenic plants transformed with the same exogenous gene.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (USA)* 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters-need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

Specific Promoter: In the context of the current invention, "specific promoters" refers to promoters that have a high preference for being active in a specific tissue or cell and/or at a specific time during development of an organism. By "high preference" is meant at least 3-fold, preferably 5-fold, more preferably at least 10-fold still more preferably at least 20-fold, 50-fold or 100-fold increase in transcription in the desired tissue over the transcription in any other tissue. Typical examples of temporal and/or tissue specific promoters of plant origin that can be used with the polynucleotides of the present invention, are: (get ref for germination specific); RCc2 and RCc3, promoters that direct root-specific gene transcription in rice (Xu et al., *Plant Mol. Biol.* 27:237 (1995) and TobRB27, a root-specific promoter from tobacco (Yamamoto et al., *Plant Cell* 3:371 (1991)).

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m=81.5-16.6(\log_{10}[Na^+])+0.41(\% \ G+C)-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6 \log\{[Na^+]/(1+0.7[Na^+])\}+0.41(\% \ G+C)-500/L0.63(\% \ \text{formamide}) \quad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools". Thus, the superpool contains an equal amount of seed from 500 different events, but only represents 100 transgenic plants with a distinct exogenous nucleotide sequence transformed into them, because the master pools are of 5 different events with the same exogenous nucleotide sequence transformed into them.

$T_0$: As used in the current application, the term "$T_0$" refers to the whole plant, explant, or callous tissue inoculated with the transformation medium.

$T_1$: As used in the current application, the term $T_1$ refers to the either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

2. Important Characteristics of the Polynucleotides and Polypeptides of the Invention The polynucleotides and polypeptides of the present invention are of interest because when they are misexpressed (i.e. when expressed at a non-natural location or in an increased or decreased amount) they produce plants with modified biomass. "Modified biomass" is a term that includes various responses to environmental or developmental conditions that affect the growth and development of the plant. For example, biomass can be altered by changes in the size and number of leaves, delays or increases in flowering time, or changes in the mass of particular plant parts (e.g. stems, inflorescences, etc.) to name but a few.

The polynucleotides and polypeptides of the invention, as discussed below and as evidenced by the results of various experiments, are useful for modifying biomass. These traits can be used to exploit or maximize plant products for agricultural, ornamental or forestry purposes in different environmental or developmental growth conditions. Modulating the expression of the nucleotides and polypeptides of the present invention leads to transgenic plants that will produce increased biomass, resulting in better yields. These transgenic plants lead to reduced costs for the farmer and better yield.

3. The Polynucleotides and Polypeptides of the Invention

The polynucleotides of the invention, and the proteins expressed thereby, are set forth in the Sequence Listing. Some of these sequences are functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity and generally share at least one biochemical and/or phenotypic activity. For example, biochemical functionally comparable proteins are proteins that act on the same reactant to give the same product.

Another class of functionally comparable proteins is phenotypic functionally comparable proteins. The members of this class regulate the same physical characteristic, such as increased drought tolerance. Proteins can be considered phenotypic functionally comparable proteins even if the proteins give rise to the same physical characteristic, but to a different degree.

The polypeptides of the invention also include those comprising the consensus sequences described in the Sequence Listing. A consensus sequence defines the important conserved amino acids and/or domains within a polypeptide. Thus, all those sequences that conform to the consensus sequence are suitable for the same purpose. Polypeptides comprised of a sequence within and defined by one of the consensus sequences can be utilized for the purposes of the invention namely to make transgenic plants with improved tolerance to heat or high or low water conditions.

4. Use of the Polynucleotides and Polypeptides to make Transgenic Plants

To use the sequences of the present invention or a combination of them or parts and/or mutants and/or fusions and/or variants of them, recombinant DNA constructs are prepared which comprise the polynucleotide sequences of the invention inserted into a vector, and which are suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);
(b) YAC: Burke et al., Science 236:806-812 (1987);
(c) PAC: Stemberg N. et al., Proc Natl Acad Sci U S A. January;87(l):103-7 (1990);
(d) Bacteria-Yeast Shuttle Vectors: Bradshaw et al., Nucl Acids Res 23: 4850-4856 (1995);
(e) Lambda Phage Vectors: Replacement Vector, e.g., Frischauf et al., J. Mol Biol 170: 827-842 (1983); or Insertion vector, e.g., Huynh et al., In: Glover NM (ed) DNA Cloning: A practical Approach, Vol. 1 Oxford: IRL Press (1985); T-DNA gene fusion vectors :Walden et al., Mol Cell Biol 1: 175-194 (1990); and
(g) Plasmid vectors: Sambrook et al., infra.

Typically, the construct comprises a vector containing a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as p326 or CaMV35S. Alternatively, the plant promoter directs transcription of a sequence of the invention in a specific tissue manner (tissue-specific promoter) or is otherwise under more precise environmental control (inducible promoter). Various plant promoters, including constitutive, tissue-specific and inducible, are known to those skilled in the art and can be utilized in the present invention. Typically, preferred promoters to use in the present invention are those that are induced by heat or low water conditions Such as the RD29a promoter (Kasuga et al., *Plant Cell Physiol.* 45:346 (2004) and Yamaguchi-Shinozaki and Shinozali, *Mol Gen Genet.* 236: 331 (1993)) or other DRE-containing (dehydration-responsive elements) promoters (Liu et al, Cell 10: 1391 (1998)). Another preferred embodiment of the present invention is the use of root specific promoters such as those present in the AtXTH17, AtXTH18, AtXTH19 and AtXTH20 genes of *Arabidopsis* (Vissenberg et al. (2005) *Plant Cell Physiol* 46:192) or guard cell specific promoters such as TGG1 or KST1 (Husebye et al. (2002) *Plant Physiol* 128:1180; Plesch et al. (2001) *Plant J* 28:455).

Alternatively, misexpression can be accomplished using a two component system, whereby the first component comprises a transgenic plant comprising a transcriptional activator operatively linked to a promoter and the second component comprises a transgenic plant comprising a sequence of the invention operatively linked to the target binding sequence/region of the transcriptional activator. The two transgenic plants are crossed and the sequence of the invention is expressed in their progeny. In another alternative, the misexpression can be accomplished by transforming the sequences of the two component system into one transgenic plant line.

Any promoter that functions in plants can be used in the first component, such as those discussed above. Suitable transcriptional activator polypeptides include, but are not limited to, those encoding HAP1 and GAL4. The binding sequence recognized and targeted by the selected transcriptional activator protein (e.g. a UAS element) is used in the second component.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al., *Ann. Rev. Genet.* 22:421 (1988); and Christou, Euphytica, v. 85, n.1-3:13-27, (1995).

Processes for the transformation and regeneration of monocotyledonous and dicotyledonous plants are known to the person skilled in the art. For the introduction of DNA into a plant host cell a variety of techniques is available. These techniques include transformation of plant cells by injection (e.g. Newell, 2000), microinjection (e.g. Griesbach (1987) *Plant Sci.* 50 69-77), electroporation of DNA (e.g. Fromm et al. (1985) *Proc. Natl Acad. Sci. USA* 82:5824 and Wan and Lemaux, Plant Physiol. 104 (1994), 37-48), PEG (e.g. Paszkowski et al. (1984) *EMBO J.* 3:2717), use of biolistics (e.g. Klein et al. (1987) *Nature* 327:773), fusion of cells or protoplasts (Willmitzer, L., 1993 Transgenic plants. In: Biotechnology, A Multi-Volume Comprehensive Treatise (H.J. Rehm, G. Reed, A. Pühler, P. Stadler, eds., Vol. 2, 627-659, VCH Weinheim-New York-Basel-Cambridge), via T-DNA using *Agrobacterium tumefaciens* (e.g. Fraley et al. (Crit. Rev. Plant. Sci. 4, 1-46 and Fromm et al., Biotechnology 8 (1990), 833-844) or *Agrobacterium rhizogenes* (e.g. Cho et al. (2000) *Planta* 210:195-204) or other bacterial hosts (e.g. Brootghaerts et al. (2005) Nature 433:629-633), as well as further possibilities.

In addition, a number of non-stable transformation methods well known to those skilled in the art may be desirable for the present invention. Such methods include, but are not limited to, transient expression (e.g. Lincoln et al. (1998) *Plant Mol. Biol. Rep.* 16:14) and viral transfection (e.g. Lacomme et al. (2001) In "Genetically Engineered Viruses" (C. J. A. Ring and E. D. Blair, Eds). Pp. 59-99, BIOS Scientific Publishers, Ltd. Oxford, UK).

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased biomass, without reduction in fertility, on essentially any plant.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospennae are Pinales, Ginkgoales, Cycadales and Gnetales.

The method of the invention is preferably used with plants that are interesting for agriculture, horticulture, biomass for bioconversion and/or forestry. Examples are tobacco, oilseed rape, sugar beet, potato, tomato, cucumber, pepper, bean, pea, citrus fruit, apple, pear, berries, plum, melon, eggplant, cotton, soybean, sunflower, rose, poinsettia, petunia, guayule, cabbage, spinach, alfalfa, artichoke, corn, wheat, rye, barley, grasses such as switch grass or turf grass, millet, hemp, banana, poplar, eucalyptus trees, conifers.

Homologs Encompassed by the Invention

Agents of the invention include proteins comprising at least about a contiguous 10 amino acid region preferably comprising at least about a contiguous 20 amino acid region, even more preferably comprising at least about a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Due to the degeneracy of the genetic code, different nucleotide codons may be used to code for a particular amino acid. A host cell often displays a preferred pattern of codon usage. Nucleic acid sequences are preferably constructed to utilize the codon usage pattern of the particular host cell. This generally enhances the expression of the nucleic acid sequence in a transformed host cell. Any of the above described nucleic acid and amino acid sequences may be modified to reflect the preferred codon usage of a host cell or organism in which they are contained. Modification of a nucleic acid sequence for optimal codon usage in plants is described in U.S. Pat. No. 5,689,052. Additional variations in the nucleic acid sequences may encode proteins having equivalent or superior characteristics when compared to the proteins from which they are engineered.

It is understood that certain amino acids may be substituted for other amino acids in a protein or peptide structure (and the nucleic acid sequence that codes for it) without appreciable change or loss of its biological utility or activity. The amino acid changes may be achieved by changing the codons of the nucleic acid sequence.

It is well known in the art that one or more amino acids in a native sequence can be substituted with other amino acid(s), the charge and polarity of which are similar to that of the native amino acid, i.e., a conservative amino acid substitution, resulting in a silent change. Conservative substitutes for an amino acid within the native polypeptide sequence can be selected from other members of the class to which the amino acid belongs (see below). Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

In a further aspect of the present invention, nucleic acid molecules of the present invention can comprise sequences that differ from those encoding a protein or fragment thereof selected from the group consisting of the sequences presented in the Sequence Listing due to the fact that the different nucleic acid sequence encodes a protein having one or more conservative amino acid changes.

In another aspect, biologically functional equivalents of the proteins or fragments thereof of the present invention can have about 10 or fewer conservative amino acid changes, more preferably about 7 or fewer conservative amino acid changes, and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

5. Experiments Confirming the Usefulness of the Polynucleotides and Polypeptides of the Invention 5.1 Procedures The nucleotide sequences of the invention were identified by use of a variety of screens for increased biomass. These screens are recognized by those skilled in the art to be predictive of nucleotide sequences that provide plants with modified biomass because they result in modification of particular organs or developmental characteristics. These screens generally fall into two categories (1) soil screens and (2) in vitro screens.

Soil screens have the advantage of assaying the response of the entire plant. On the other hand, in vitro screens have the advantage of relying on defined media and so allow more defined manipulation of growth conditions.

In general, the screens used to identify the polynucleotides and polypeptides of the invention were conducted using the individual events of the $T_1$ transformed plants. The $T_1$ plants were transformed with a Ti plasmid containing a particular SEQ ID NO in the sense orientation relative to a constitutive promoter and harboring the plant-selectable marker gene phosphinothricin acetyltansferase (PAT), which confers herbicide resistance to transformed plants. The results of the screens conducted for each SEQ ID NO can be found in the Examples below.

1. Quantitative Morphology Measurements

Screens for altered morphology identify plants that have altered biomass.

Approximately 0.2 ml of seed are sown per pot containing soil of the following composition: 60% autoclaved Sunshine Mix #5, 40% vermiculite with 2.5 Tbsp Osmocote and 2.5 Tbsp 1% granular Marathon per 25 L of soil. After sowing, pots are covered with plastic propagation domes and seed is placed at 4° C. in the dark for at least 3 days. Pots are then returned to the greenhouse (long-day light conditions of 16 hours) and covered with 55% shade cloth. When the cotyledons have fully expanded both the domes and shade cloth are removed.

Plants are sprayed with a mixture of 3 ml Finale in 48 oz of water. Spraying is repeated every 3-4 days until only transformants remain. The remaining transformants were weeded to a maximum of 5 evenly spaced transformants per pot.

Seedlings were screened at 4 developmental stages: seedling, rosette, flowering and senescence using the following criteria:

Seedling—the time after the cotyledons have emerged, but before the $3^{rd}$ true leaf begins to form.

Rosette—the time from the emergence of the $3^{rd}$ true leaf through just before the primary bolt begins to elongate.

Flowering—the time from the emergence of the primary bolt to the onset of senescence.

Senescence—the time following the onset of senescence.

$T_2$ seed is collected from the mature scenescent plants and planted and grown essentially as described above. In this case, however, only one seed, and therefore one plant were grown per pot. Measurements are taken for the following phenotypes:

Specific Phenotype: Large (including delayed flowering plants)
1. Days to Bolt=number of days between sowing of seed and emergence of first inflorescence.
2. Number of Leaves=number of rosette leaves present at date of first bolt.
3. Rosette Area=Area of rosette at time of emergence of first inflorescence, using $((LxW)*3.14)/4$.
4. Primary Inflorescence Thickness=diameter of primary inflorescence 2.5 cm up from base. This measurement was taken at the termination of flowering/onset of senescence.
5. Height=length of longest inflorescence from base to apex. This measurement was taken at the termination of flowering/onset of senescence.

DNA is isolated from each $T_2$ plant and used in PCR reactions using the following cycling conditions: 95° C. for 5 min, 35 cycles of (94° C. for 30 sec, then 59° C. for 30 sec, then 72° C. for 1 min), 72° C. for 8 min and 4° C. hold. Aliquots of the reaction product are analyzed on a 1.0% agarose gel stained with ethidium bromide. This process is done to test the segregating $T_2$ plants to determine which plants contain the insert and which do not.

5.2 Results

The results of the above experiments are set forth below wherein each individual example relates to all of the experimental results for a particular polynucleotide/polypeptide if the invention.

EXAMPLE 1

Ceres cDNA 13487605

Clone 12272, Ceres cDNA 13487605, encodes an unknown protein from *Arabidopsis thaliana*.

Ectopic expression of Ceres cDNA 13487605 under the control of the CaMV35S promoter induces a number of phenotypes including:
Thicker inflorescences
Larger rosettes
Increased rosette leaf number
Delayed flowering Generation and Phenotypic Evaluation of $T_1$ and $T_2$ Lines Containing 35S::cDNA 13487605.

Wild-type *Arabidopsis* Wassilewskija (WS) plants were transformed with a Ti plasmid containing cDNA 13487605 in the sense orientation relative to the 35S constitutive promoter. The $T_i$ plasmid vector used for this construct, CRS338, contains PAT and confers herbicide resistance to transformed plants. Twenty independently transformed events were selected and evaluated for their qualitative phenotype in the $T_1$ generation. No negative phenotypes were observed in the $T_1$ plants.

$T_2$ measurements taken were:
Days to bolt=number of days between sowing of seed and emergence of first inflorescence.
Rosette Leaf Number at Bolt=number of rosette leaves present at time of emergence of first inflorescence.
Rosette Area=area of rosette at time of initial inflorescence emergence, using formula $((LxW)*3.14)/4$.
Primary Inflorescence Thickness=diameter of primary inflorescence 2.5 cm up from base. This measurement was taken at the termination of flowering/onset of senescence.
Height=length of longest inflorescence from base to apex. This measurement was taken at the termination of flowering/onset of senescence.

Results:

Qualitative Analysis of the $T_1$ Plants

Four of the 20 events (ME04524-01 to ME04524-30) produced larger rosettes with more leaves and thicker inflorescences compared to the controls. These plants were also delayed in flowering time and had no fertility defects. Four other events were delayed in flowering, but did not exhibit a significant increase in size or leaf number (Table 1). The transgenic "control" was a set of plants expressing a different 35S::cDNA fusion and which were indistinguishable from the untransformed WS wildtype.

TABLE 1

Qualitative phenotypes observed in 35S::cDNA 13487605 $T_1$ events (highlighted events were chosen for $T_2$ evaluation)

| Event | Increased Rosette Size Increased Inflorescence Thickness | Late Flowering |
|---|---|---|
| ME04524-01 | X | X |
| ME04524-02 | X | X |
| ▓▓▓▓▓▓▓▓ | ▓▓▓▓▓▓▓▓ | ▓▓▓▓▓▓▓▓ |
| ▓▓▓▓▓▓▓▓ | ▓▓▓▓▓▓▓▓ | ▓▓▓▓▓▓▓▓ |

TABLE 1-continued

Qualitative phenotypes observed in 35S::cDNA 13487605 T$_1$ events
(highlighted events were chosen for T$_2$ evaluation)

| Event | Increased Rosette Size | Increased Inflorescence Thickness | Late Flowering |
|---|---|---|---|
| ME04524-05 | | | |
| ME04524-06 | | | X |
| ME04524-07 | | | X |
| ME04524-08 | | | |
| ME04524-09 | | | |
| ME04524-10 | | | |

TABLE 1-continued

Qualitative phenotypes observed in 35S::cDNA 13487605 T$_1$ events
(highlighted events were chosen for T$_2$ evaluation)

| Event | Increased Rosette Size | Increased Inflorescence Thickness | Late Flowering |
|---|---|---|---|
| ME04524-21 | | | |
| ME04524-22 | | | |
| ME04524-23 | | | |
| ME04524-24 | | | |
| ME04524-25 | | | |
| ME04524-26 | | | X |
| ME04524-27 | | | |
| ME04524-28 | | | |
| ME04524-29 | | | X |
| ME04524-30 | | | |

Quantitative Analysis of the T$_2$ Plants:

Events ME04524-03 and ME04524-04 were evaluated in greater detail in the T$_2$ generation. Eighteen individuals were sown and observed for both events. The transgenic plants showed a 0.05 level of statistical significance for increased primary inflorescence thickness, increased number of rosette leaves, a larger rosette, and delay of flowering time (Tables 2-4). All plants noted in the table as ME04524-03 and ME04524-04 were segregating progeny of the T$_1$ which exhibited the phenotype of interest. All plants noted in the table as -03 or -04 Control were T$_2$ segregating progeny which did not exhibit the phenotype and did not contain the transgene (internal controls). Total seed yield was not measured for these plants.

Event ME04524-03 had all 13 transgene-containing plants exhibiting the beneficial phenotype. Event ME04524-04 had 8 transgene-containing plants which exhibited the beneficial phenotype and 3 transgene-containing plants which appeared wild-type. Event ME04524-04 also had 4 plants which exhibited a much more severe phenotype. These plants were severely dwarfed, but the dwarf phenotype is likely due to a dosage or homozygous insert/knockout effect. Statistical analyses compared the internal controls to the plants which contained the transgene and beneficial phenotype. All transgene-containing plants with a wild-type phenotype and dwarf plants were omitted from the statistical analyses in Table 2.

As the phenotype is qualitative, plants were divided into two classes and a Chi-square comparison test was conducted. In the Chi-square comparison test, significance can be assessed with fewer than 5 controls and can be determined to a 0.05 level of significance (Tables 3-4). For this test, "Large Plant" is the category of plants with increased primary inflorescence thickness, increased height, increased number of rosette leaves, a larger rosette, and delay of flowering time. "Wild-type" is the category of plants which do not appear different than the internal control. The means are presented in Table 2.

TABLE 2

Quantitative phenotypes observed in 35S::cDNA 13487605 T$_2$ events

| Event/Control | Number of Observations | Rosette Area (mm$^2$) | Number of Leaves | Height (cm) | Primary Inflorescence Thickness (mm) | Days to Bolt |
|---|---|---|---|---|---|---|
| ME04524-03 | 13 | 2682.4 | 8.2 | 47.7 | 1.48 | 19.6 |
| -03 Control | 5 | 2057.8 | 6.4 | 52.2 | 1.09 | 17.0 |
| ME04524-04 | 8 | 3444.1 | 9.6 | 50.1 | 1.67 | 22.8 |
| -04 Control | 3 | 2055.7 | 6.3 | 39.9 | 1.34 | 17.3 |

TABLE 3

Chi-square comparison test. Significant phenotypic
differences between ME04524-03 and internal controls
(>0.05 level of significance)

| | Large Plant | | Wild-type | | |
|---|---|---|---|---|---|
| | # Observed | # Expected | # Observed | # Expected | Total |
| No Insert | 0 | 3.6 | 5 | 1.4 | 5 |
| Contains Insert | 13 | 9.4 | 0 | 3.6 | 13 |
| Total | 13 | | 5 | | 18* |
| | Chi-square = 18.00* | | | | |

*Significant at the 0.01 level.

TABLE 4

Chi-square comparison test. Significant phenotypic
differences between ME04524-04 and internal controls
(Greater than 0.05 level of significance)

| | Large Plant | | Wild-type | | |
|---|---|---|---|---|---|
| | # Observed | # Expected | # Observed | # Expected | Total |
| No Insert | 0 | 2.3 | 3 | 0.7 | 3 |
| Contains Insert | 8 | 10.7 | 3 | 3.3 | 11 |
| Total | 8 | | 6 | | 14 |
| | Chi-square = 5.09** | | | | |

**Significant at the 0.025 level.

Table 5 provides the result of the consensus sequence analysis based on Ceres cDNA 13487605. Table 5 recites CeresClone:320985 (SEQ ID No. 4); gi|50947369 (SEQ ID No. 6); CeresClone:246369 (SEQ ID No. 5); Lead clone12272 (SEQ ID No. 2); and CeresClone:541471 (SEQ ID No. 3) and the consensus sequences, including the amino acid sequences that comprise the consensus sequence, among which are SEQ ID NOs. 9-25.

TABLE 5

/tmp/289358.aln

```
CeresClone: 320985    M L S D Q E L A Q Y   V E S L V Q H T A A   Q G G T - - - - G   I S A D A V V R Q L   G A Q L G V D L S P    45
gi|50947369           M L S D Q E L A R Y   V E S F V R Q A A A   V P G A V A A A G G   I S A E S V A R Q L   G P Q L G L D L T P    50
CeresClone: 246369    M V S D Q E I A S C   V E S V L R G S A G   G P G E - - - - -   V S L T A V L Q Q A   E A T L G V D L S H    44
Lead-clone 12272      M V S D Q D L A K G   V E T L L R Q S - -   D P S S - - - - L   T S L S S I V Q Q L   E A K L G L D L T E    43
CeresClone: 541471    M V T D Q D I A K G   V E S L L R H S - -   D P N S - - - - I   T V N G V V Q Q L   E A K L G L D L S H    43

Consensus             M V S D Q E L A K -   V E S L L R - S A -   - P G S - - - - -   V S L - - V V Q Q L   E A - L G L D L S -    50

CeresClone: 320985    K A Q L T R S V L V   A L L G P A A A A P A   P D P A G S R K D P   F D P A T A A A A G   G P R A E T P P Q Q    95
gi|50947369           K A P L I R D L L L   A L F S P - - - - -   - - - - - - - - -   - - - - - - - - -   - P P Q G A P F T S    74
CeresClone: 246369    K A G F I R D Q M D   L F F G P - - - - -   - - - - - - - - -   - - - - - - - - -   - R L Q P Q P L T T    68
Lead-clone 12272      K T T F I R D Q I N   I L L R A - - - - -   - - - - - - - - -   S A S V A S A S S V   Q Q S H P P P P P S    82
CeresClone: 541471    K A S F I R D Q I D   H L L R S - - - - -   - - H Q N P - - - -   - - - - - - - - -   - - - - - - - - -    58

Consensus             K A - F I R D Q - D   - L L - P - - - - -   - - - - - - - - -   - - - - - - - - -   - - - - - - - P - S   100

CeresClone: 320985    M H F S T A A A I S S   A P A P S P A V P H   F F - P Q Q H Q H Q   M Q Y F L S A P Q Q   Y Q H Q Q Q Q Q R A   144
gi|50947369           S A P S I P S L A S -   A S A S A A A A G H   F F S - Q Q Q H Q Q   L Q T E L T A S Q Q   Y Q H R G G A G A A   124
CeresClone: 246369    P Q L A P P P P Q A   V V A P A D A V P Q   - - Q P Q P H Q V -   L P Q A P P S A Q Q   M Q P Q Q L A P - -   113
Lead-clone 12272      S H Q Q Q N L H S G   V N V P P M A K G H   F T L S H P S Q - -   - F S V S S S Q S   Q Q - - - - - - - -   119
CeresClone: 541471    - - - Q P Q T F     A P H P P L H K D   Y F A P H T Q L H -   - E P T T H - - -   - - - - - - - - -    87

Consensus             - - - S - - - S S   A - A P A - A - - H   F F - P Q - Q Q - -   L - - F - T - S Q Q   - Q - - - - - - -   150

CeresClone: 320985    G A S P S P F D I P   A - - S Y R Y G H   Q P L P Q A D Q A Q   L Q R L V - - - -   - Q L Q H Q Q Q Q Q   184
gi|50947369           A A P S A Y G V A   A A A A G Y R Y - G   Q P F P Q D E G A H   L Q R L V Q M H H H   Q Q Q Q Q Q Q Q Q Q   173
CeresClone: 246369    L Q P Q L M F Q T I   H Q L P A T S - -   - P V P P V V S A P P   A M A F - - - - -   - Y P P P P L A F   151
Lead-clone 12272      Y P S H F A L Q P P   Y H S Y D L N F I - R   Q P Y P P V Y M P P Q   Q H Q H - - - -   - Q Q Q S P R Q Q   160
CeresClone: 541471    F A P H F A L H D -   - E I N F L Q - - -   H P H P - - - - -   P R K V - - - - -   - E T F P P Q N -   119

Consensus             - A P - - A F - -   - - - - - I N - - -   Q P - P - - - - -   - Q R L - - - - -   - Q - Q - P Q Q Q   200
```

TABLE 5-continued

| | | | | | | |
|---|---|---|---|---|---|---|
| CeresClone: 320985 | L A A A A R V A A A | A A P T P G E S P R | A P E P P P A P A P | A A S K K - - N S | S A S V G A K R K G | 231 |
| gi\|50947369 | Q M A A A A G V A | A A P - - - - - - | - P T A V E S P R P | A A A S K - - - K E | S A S T G V K R R G | 212 |
| CeresClone: 246369 | R Y T T G L A G A | T G G T V S F Q Q P | - A P G A G G T A S P | T A A P Q V A G D N | K E S S K R R R G | 201 |
| Lead-clone 12272 | Q S S V M L S H G G | N A S - - - - - - | - L S V N Q A P K - | - - - - - E - | S A P A G T K R K G | 192 |
| CeresClone: 541471 | - - - - - - - - | - - - - - - - - | - V A P P Q V P K - | - - - - - - - | S V Q T G S K R R G | 138 |
| Consensus | Q - - - - A - - A | - A - - - - - - | - P - - - Q - P K P | - A A - K - - - E | S A S - G - K R R G | 250 |
| CeresClone: 320985 | G P G G L N K V C G | V S P E L Q A I V G | E P A M A R T E I V | K Q L W A Y I R R N | N L Q D P N N K R K | 281 |
| gi\|50947369 | G P G G L N K V C G | V S P E L Q A I V G | E P T M A R T E I V | K Q L W A Y I R R N | N L Q D P D D K R K | 262 |
| CeresClone: 246369 | G P G G L N K V C G | I S P E L Q T I V G | E T A M S R T Q I V | K Q L W A Y I R Q N | N L Q D P S N K R K | 251 |
| Lead-clone 12272 | G P G G L N K V C R | V S P E L E V V V G | E P A L P R T E I V | R Q L W A Y I K K N | N L Q D P G N K R K | 242 |
| CeresClone: 541471 | G A G G L N K V C G | V S P E L Q A V V G | E P A M A R T E I V | K Q L W A Y I R - N | N L Q D P N N K R K | 188 |
| Consensus | G P G G L N K V C G | V S P E L Q A I V G | E P A M A R T E I V | K Q L W A Y I R - N | N L Q D P N N K R K | 300 |
| CeresClone: 320985 | I I C N D E L R L V | F E T D S T D M F Q | M N K L L S K H I R | P L E S K N D S K P | E A K K L P - - - | 328 |
| gi\|50947369 | I I C N D E L R L V | F E T D S T D M F K | M N K L L A K H I T | P L E A K K D S N R | D S K K L K - - - | 309 |
| CeresClone: 246369 | I I C D D A L R V V | F E T D T D D M F K | M N K L L A K H I L | P L D P K S Q L H - | E V K R M K A P T - | 299 |
| Lead-clone 12272 | I I C D D A L R L V | F E T D C T D M F K | M N K L L A K F I I | P L D P S K D S G - | Q A K K A K T E V E | 291 |
| CeresClone: 541471 | G A G G L N K V C R | F E T D C T D M F K | M N Q L L A K H I - | P L G P T K E S - | Q A K R V K V D T E | 236 |
| Consensus | I I C N D E L R L V | F E T D S T D M F K | M N K L L A K H I - | P L - P K K D S - | - A K K L K - - - | 350 |
| CeresClone: 320985 | Q G D E P I S S V E | T D V N Q L P L M V | S D A L A T F F G T | G E R E M V H S E A | V K R V W D H I K S | 378 |
| gi\|50947369 | V D S E P I S P A E | T D V N Q L P I I L | S D A L A K F F G T | G E K E M P S S E A | V K R V W K D S N R | 359 |
| CeresClone: 246369 | M S P Q P G R P I D | - - - Q P S I V I | D G T - F P Q D D A | D G T - F P Q D D A | L K Y L W D Y I K A | 344 |
| Lead-clone 12272 | T K T E T T E P V S | S T A I S S T V T L | S E P L G K F F G T | G E T E M A D E E L | I R R V W E Y I K L | 341 |
| CeresClone: 541471 | I K T E S A E P A - | - - P S T V A L | S E A L A K F F G T | E G R E M Q Q S E A | I V W E Y I K L | 281 |
| Consensus | - - T E P - - P V E | T - - - Q - T - - | S D A L A K F F G T | G E R E M - - S E A | - K R V W D Y I K S | 400 |
| CeresClone: 320985 | N D L E D P E N P T | V I L C D S K L K Q | L F G R E S L T A H | G V S E L L - S D H | L Y T Q S T N I | 425 |
| gi\|50947369 | N N L E D P A N P T | M I L C D S K L K Q | L F G C E S L T A V | S V S E L L - S Q H | L F K Q P N K L - - - | 406 |
| CeresClone: 246369 | - I L C D S K L Q E | - I L C D S K L Q E | L L G C E S I P M S | G L S E M L - G H H | F I K K T - - - | 387 |
| Lead-clone 12272 | N H L E D P V N P M | A I Q C D E K L R D | L G C E S I S A V | G I N E M L - R R H | M Y K Q S - - - | 385 |
| CeresClone: 541471 | H H L E D P L N S M | V I L C D A K L Q E | L L G C E S I S A L | G I P E M L A R H H | L F K Q S D T R | 329 |
| Consensus | N N L E D P - N P T | V I L C D S K L - - | L F G C E S I - A V | G - S E M L - - - H | L - K Q S - - - | 448 |

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

What is claimed is:

1. A plant which comprises an introduced isolated nucleic acid molecule which encodes an amino acid sequence having at least 95% identity to SEQ ID NO:2, wherein expression of said nucleic acid molecule increases biomass of said plant as compared to a wild-type plant cultivated under the same conditions.

2. A method for increasing biomass in a plant comprising
   a) transforming a plant cell with an isolated nucleic acid molecule which encodes an amino acid sequence having at least 95% identity to SEQ ID NO:2;
   b) generating from said plant cell a transformed plant in which said nucleic acid molecule is overexpressed: and
   c) selecting from a plurality of said transformed plants a plant having increased plant size, increased vegetative growth, modulated plant architecture and/or increased biomass as compared to a control plant that does not comprise said nucleic acid molecule.

3. A transgenic plant having a gene construct comprising a nucleic acid molecule encoding an amino acid sequence having at least 95% identity to SEQ ID NO:2, wherein the nucleic acid molecule is operably linked to a plant promoter so that the nucleic acid molecule is ectopically overexpressed in the transgenic plant, and the transgenic plant exhibits:
   i) greater fresh or dry weight at maturation, or
   ii) delayed flowering
than a progenitor plant which does not contain the gene construct, when the transgenic plant and the progenitor plant are cultivated under identical environmental conditions.

4. The plant according to claim 1 or 3, wherein said nucleic acid molecule encodes an amino acid sequence exhibiting at least 96% sequence identity to SEQ ID NO:2.

5. The method of claim 2, wherein said nucleic acid molecule has the sequence set forth in SEQ ID NO:1.

6. The method according to claim 2, wherein said nucleic acid molecule encodes the amino acid sequence set forth in SEQ ID NO: 2.

7. The plant according to claim 1 or 3, wherein said nucleic acid molecule encodes an amino acid sequence exhibiting at least 97% sequence identity to SEQ ID NO:2.

8. The plant according to claim 1 or 3, wherein said nucleic acid molecule encodes the amino acid sequence according to SEQ ID NO:2.

9. The plant according to claim 1 or 3, wherein said nucleic acid molecule encodes an amino acid sequence exhibiting at least 98% sequence identity to SEQ ID NO:2.

10. The plant according to claim 1 or 3, wherein said nucleic acid molecule encodes an amino acid sequence having at least 99% identity to SEQ ID NO:2.

11. The method according to claim 2, wherein said nucleic acid molecule encodes an amino acid sequence exhibiting at least 97% sequence identity to SEQ ID NO. 2.

12. The method according to claim 2, wherein said nucleic acid molecule encodes an amino acid sequence exhibiting at least 98% identity to SEQ ID NO:2.

13. The method according to claim 2, wherein said nucleic acid molecule encodes an amino acid sequence exhibiting at least 99% identity to SEQ ID NO:2.

14. A plant having increased plant size, increased vegetative growth, modulated plant architecture and/or increased biomass comprising a gene construct comprising a nucleic acid molecule which encodes an amino acid sequence having at least 95% identity to SEQ ID NO:2, wherein the nucleic acid molecule is operably linked to a plant promoter so that the nucleic acid molecule is ectopically overexpressed in the plant, wherein said plant is obtained by:
   a) transforming a plant cell with a nucleic acid molecule which encodes an amino acid sequence having at least 95% identity to SEQ ID NO:2;
   b) generating from said plant cell a transformed plant in which said nucleic acid molecule is overexpressed; and
   c) selecting from a plurality of said transformed plants a plant having increased plant size, increased vegetative growth, modulated plant architecture and/or increased biomass as compared to a control plant that does not comprise said nucleic acid molecule.

15. A plant cell, plant material or seed of the plant of claim 1 or 3, wherein the plant cell, plant material or seed comprise said nucleic acid molecule.

16. A plant cell, plant material or seed of the plant of claim 4, wherein the plant cell, plant material or seed comprise said nucleic acid molecule.

17. A plant cell, plant material or seed of the plant of claim 7, wherein the plant cell, plant material or seed comprise said nucleic acid molecule.

18. A plant cell, plant material or seed of the plant of claim 9, wherein the plant cell, plant material or seed comprise said nucleic acid molecule.

19. A plant cell, plant material or seed of the plant of claim 10, wherein the plant cell, plant material or seed comprise said nucleic acid molecule.

20. A plant cell, plant material or seed of the plant of claim 8, wherein the plant cell, plant material or seed comprise said nucleic acid molecule.

21. A plant cell, plant material or seed of the plant of claim 14, wherein the plant cell, plant material or seed comprise said nucleic acid molecule.

* * * * *

SEQUENCE LISTING

```
<160> NUMBER OF SEQ ID NOS: 8

<210> SEQ ID NO 1
<211> LENGTH: 1533
<212> TYPE: DNA
<213> ORGANISM: Arabidopsis thaliana

<400> SEQUENCE: 1
aaaaaaagct tgaaattct ctctcgacaa tggtgtcgga ccaggatcta gcgaaaggag      60 tcgagactt gcttcgacaa tccgacccta gctctctcac atcgttaagc agtattgttc     120
agcagcttga agctaagtta gggttagacc tcacggagaa gacgactttc atcagagatc    180
agatcaatat cctcctccgt gctcaccaaa acccttctgc ctccgtcgcc tccgcttcat    240
ccgtacaaca atctcaccct cctcctccgc cgtcttctca ccagcagcag aatttgcatt    300
ccggcgtcaa tgttcctccg atggcgaaag gcatttcac acttagccat ccttcgcaat     360
tctctgtttc ttctcaatca caacaatatc cttcacattt cgctcttcag cctccttatc    420
actcttatga cctaaatttc cggcagcctt atccggttta catgccgccg caacagcacc    480
agcatcagca gcagtctccg cgacaacaac aatcctctgt gatgctctca catggcggga    540
atgcttctct atctgttaat caagccccaa agaaagtgc tccggctgga actaaaagaa     600
agggtggtcc tggaggacta aacaaagtct gtagggtttc tccagaactt gaagtagttg    660
ttggtgaacc tgctcttcct agaactgaga ttgtgaggca attgtgggct tatataagga    720
agaataacct tcaagacccg agtaacaagc ggaagatcat ctgtgatgat gcgttgcgtg    780 tggttttga gactgattgc actgacatgt tcaagatgaa taagttgctt gctaagcata    840
ttctcccgct tgatccatca aaggactctg gtcaagcaaa aaaggcaaaa actgaggtgg    900
agactaagac tgagaccacc gagcctgtta gttcaactgc tattagttca actgttacat   960
tatctgagcc acttggtaag ttctttggca ctggtgagac ggagatggca gacgaagaga  1020
ttattcgccg tgtttgggaa tacataaaac tcaacaattt agaggaccca gtaaatccaa  1080
tggctattca gtgtgatgaa aagctccgag atcttcttgg atgtgaaagc atttcagctg   1140
tggggataaa tgagatgctg aggcgccata tgtacaagca gtcgtgatat cttctggtct   1200
gacttaatta actaggaact actagtgtgt gtatctaggg aacctactta tgactccttg   1260
ctgtagaact ctgatagga agaaaagatc ctttttcact tttaacttcc tttaatgcta   1320
ttttaatctt ccgttgggtt ctttgttta gttggttgt tatcgacatg cttaggttga    1380
tgttgtattt agtattgtac cgaaactcta gtgttaaggg tgaaacggcg cagatgtttt  1440
gtattaaacg ccattcaccc atgaatgtct taggaaaaaa aaactcatgt gtttaactat  1500
gttttccctg ttggaaatat ttgcatccta ctg                              1533

<210> SEQ ID NO 2
<211> LENGTH: 385
<212> TYPE: PRT
<213> ORGANISM: Arabidopsis thaliana

<400> SEQUENCE: 2
```

```
Met Val Ser Asp Gln Asp Leu Ala Lys Gly Val Glu Thr Leu Leu Arg
 1               5                  10                  15

Gln Ser Asp Pro Ser Ser Leu Thr Ser Leu Ser Ser Ile Val Gln Gln
             20                  25                  30

Leu Glu Ala Lys Leu Gly Leu Asp Leu Thr Glu Lys Thr Thr Phe Ile
         35                  40                  45

Arg Asp Gln Ile Asn Ile Leu Leu Arg Ala His Gln Asn Pro Ser Ala
 50                  55                  60

Ser Val Ala Ser Ala Ser Ser Val Gln Gln Ser His Pro Pro Pro
 65              70                  75                  80

Pro Ser Ser His Gln Gln Asn Leu His Ser Gly Val Asn Val Pro
             85                  90                  95

Pro Met Ala Lys Gly His Phe Thr Leu Ser His Pro Ser Gln Phe Ser
            100                 105                 110

Val Ser Ser Gln Ser Gln Gln Tyr Pro Ser His Phe Ala Leu Gln Pro
            115                 120                 125

Pro Tyr His Ser Tyr Asp Leu Asn Phe Arg Gln Pro Tyr Pro Val Tyr
        130                 135                 140

Met Pro Pro Gln Gln His Gln His Gln Gln Ser Pro Arg Gln Gln
145                 150                 155                 160

Gln Ser Ser Val Met Leu Ser His Gly Gly Asn Ala Ser Leu Ser Val
                165                 170                 175

Asn Gln Ala Pro Lys Glu Ser Ala Pro Ala Gly Thr Lys Arg Lys Gly
            180                 185                 190

Gly Pro Gly Gly Leu Asn Lys Val Cys Arg Val Ser Pro Glu Leu Glu
        195                 200                 205

Val Val Val Gly Glu Pro Ala Leu Pro Arg Thr Glu Ile Val Arg Gln
210                 215                 220

Leu Trp Ala Tyr Ile Arg Lys Asn Asn Leu Gln Asp Pro Ser Asn Lys
225                 230                 235                 240

Arg Lys Ile Ile Cys Asp Asp Ala Leu Arg Val Val Phe Glu Thr Asp
                245                 250                 255

Cys Thr Asp Met Phe Lys Met Asn Lys Leu Leu Ala Lys His Ile Leu
            260                 265                 270

Pro Leu Asp Pro Ser Lys Asp Ser Gly Gln Ala Lys Lys Ala Lys Thr
        275                 280                 285

Glu Val Glu Thr Lys Thr Glu Thr Thr Glu Pro Val Ser Ser Thr Ala
            290                 295                 300

Ile Ser Ser Thr Val Thr Leu Ser Glu Pro Leu Gly Lys Phe Phe Gly
305                 310                 315                 320

Thr Gly Glu Thr Glu Met Ala Asp Glu Glu Ile Ile Arg Arg Val Trp
                325                 330                 335

Glu Tyr Ile Lys Leu Asn Asn Leu Glu Asp Pro Val Asn Pro Met Ala
            340                 345                 350

Ile Gln Cys Asp Glu Lys Leu Arg Asp Leu Leu Gly Cys Glu Ser Ile
        355                 360                 365

Ser Ala Val Gly Ile Asn Glu Met Leu Arg Arg His Met Tyr Lys Gln
370                 375                 380

Ser
385

<210> SEQ ID NO 3
<211> LENGTH: 329
<212> TYPE: PRT
```

<213> ORGANISM: Glycine max

<400> SEQUENCE: 3

Met Val Thr Asp Gln Asp Ile Ala Lys Gly Val Glu Ser Leu Leu Arg
1               5                   10                  15

His Ser Asp Pro Asn Ser Ile Thr Thr Val Asn Gly Val Val Gln Gln
                20                  25                  30

Leu Glu Ala Lys Leu Gly Leu Asp Leu Ser His Lys Ala Ser Phe Ile
            35                  40                  45

Arg Asp Gln Ile Asp His Leu Leu Arg Ser Gln Pro Gln Thr Phe Ala
        50                  55                  60

Pro His Pro Pro Leu His Lys Asp Tyr Phe Ala Pro His Thr Gln
65                  70                  75                  80

Leu His Phe Pro Thr Thr His Phe Ala Pro His Phe Ala Leu His Asp
                85                  90                  95

Glu Ile Asn Phe Leu Gln His Pro His Pro Pro Pro Arg Lys Val
                100                 105                 110

Glu Thr Phe Pro Pro Gln Asn Val Ala Pro Gln Val Pro Lys Glu
            115                 120                 125

Ser Val Gln Thr Gly Ser Lys Arg Arg Gly Gly Ala Gly Gly Leu Asn
130                 135                 140

Lys Val Cys Gly Val Ser Pro Glu Leu Gln Ala Val Val Gly Glu Pro
145                 150                 155                 160

Ala Met Pro Arg Thr Glu Ile Val Arg Gln Leu Trp Ala Tyr Ile Lys
                165                 170                 175

Lys Asn Asn Leu Gln Asp Pro Gly Asn Lys Arg Lys Ile Ile Cys Asp
                180                 185                 190

Asp Ala Leu Arg Leu Val Phe Glu Thr Asp Cys Thr Asp Met Phe Lys
            195                 200                 205

Met Asn Gln Leu Leu Ala Lys His Ile Ile Pro Leu Gly Pro Thr Lys
        210                 215                 220

Glu Ser Gln Ala Lys Arg Val Lys Val Asp Thr Glu Ile Lys Thr Glu
225                 230                 235                 240

Ser Ala Glu Pro Ala Pro Ser Thr Val Ala Ile Ser Glu Ala Leu Ala
                245                 250                 255

Lys Phe Leu Gly Thr Glu Gly Arg Glu Met Gln Gln Ser Glu Ala Ile
                260                 265                 270

Arg Leu Val Trp Glu Tyr Ile Lys Leu His His Leu Glu Asp Pro Leu
            275                 280                 285

Asn Ser Met Val Ile Leu Cys Asp Ala Lys Leu Gln Glu Leu Leu Gly
        290                 295                 300

Cys Glu Ser Ile Ser Ala Leu Gly Ile Pro Glu Met Leu Ala Arg His
305                 310                 315                 320

His Leu Phe Lys Gln Ser Asp Thr Arg
                325

<210> SEQ ID NO 4
<211> LENGTH: 425
<212> TYPE: PRT
<213> ORGANISM: Zea mays

<400> SEQUENCE: 4

Met Leu Ser Asp Gln Glu Leu Ala Gln Tyr Val Glu Ser Leu Val Gln
1               5                   10                  15

His Thr Ala Ala Gln Gly Gly Thr Gly Ile Ser Ala Asp Ala Val Val

-continued

```
                   20                  25                  30
Arg Gln Leu Gly Ala Gln Leu Gly Val Asp Leu Ser Pro Lys Ala Gln
                35                  40                  45

Leu Ile Arg Ser Val Leu Val Ala Leu Leu Gly Pro Ala Ala Ala Pro
 50                  55                  60

Ala Pro Asp Pro Ala Gly Ser Arg Lys Asp Pro Phe Asp Pro Ala Thr
 65                  70                  75                  80

Ala Ala Ala Ala Gly Gly Pro Arg Ala Glu Thr Pro Pro Gln Gln Met
                 85                  90                  95

His Phe Ser Thr Ala Ala Ala Ser Ser Ala Pro Ala Pro Ser Pro Ala
                100                 105                 110

Val Pro His Phe Phe Pro Gln Gln His Gln His Gln Met Gln Tyr Phe
                115                 120                 125

Leu Ser Ala Pro Gln Gln Tyr Gln His Gln Gln Gln Gln Arg Ala
                130                 135                 140

Gly Ala Ser Pro Ser Pro Phe Asp Ile Pro Ala Ser Tyr Arg Tyr Gly
145                 150                 155                 160

His Gln Pro Leu Pro Gln Ala Asp Gln Ala Gln Leu Gln Arg Leu Val
                165                 170                 175

Gln Leu Gln His Gln Gln Gln Leu Ala Ala Ala Arg Val Ala
                180                 185                 190

Ala Ala Ala Pro Thr Pro Gly Glu Ser Pro Arg Ala Pro Glu Pro
                195                 200                 205

Pro Pro Ala Pro Ala Pro Ala Ser Lys Asn Ser Ser Ala Ser
210                 215                 220

Val Gly Ala Lys Arg Lys Gly Pro Gly Gly Leu Asn Lys Val Cys
225                 230                 235                 240

Gly Val Ser Pro Glu Leu Gln Ala Ile Val Gly Glu Pro Ala Met Ala
                245                 250                 255

Arg Thr Glu Ile Val Lys Gln Leu Trp Ala Tyr Ile Arg Arg Asn Asn
                260                 265                 270

Leu Gln Asp Pro Asn Asn Lys Arg Lys Ile Ile Cys Asn Asp Glu Leu
                275                 280                 285

Arg Leu Val Phe Glu Thr Asp Ser Thr Asp Met Phe Gln Met Asn Lys
                290                 295                 300

Leu Leu Ser Lys His Ile Arg Pro Leu Glu Ser Lys Asn Asp Ser Lys
305                 310                 315                 320

Pro Glu Ala Lys Lys Leu Lys Pro Gln Gly Asp Glu Pro Ile Ser Ser
                325                 330                 335

Val Glu Thr Asp Val Asn Gln Leu Pro Leu Met Val Ser Asp Ala Leu
                340                 345                 350

Ala Thr Phe Phe Gly Thr Gly Glu Arg Glu Met Val His Ser Glu Ala
                355                 360                 365

Val Lys Arg Val Trp Asp His Ile Lys Ser Asn Asp Leu Glu Asp Pro
                370                 375                 380

Glu Asn Pro Thr Val Ile Leu Cys Asp Ser Lys Leu Lys Gln Leu Phe
385                 390                 395                 400

Gly Arg Glu Ser Leu Thr Ala His Gly Val Ser Glu Leu Leu Ser Asp
                405                 410                 415

His Leu Tyr Thr Gln Ser Thr Asn Ile
                420                 425

<210> SEQ ID NO 5
```

```
<211> LENGTH: 387
<212> TYPE: PRT
<213> ORGANISM: Zea mays

<400> SEQUENCE: 5

Met Val Ser Asp Gln Glu Ile Ala Ser Cys Val Glu Ser Val Leu Arg
 1               5                  10                  15

Gly Ser Ala Gly Gly Pro Gly Glu Val Ser Leu Thr Ala Val Leu Gln
            20                  25                  30

Gln Ala Glu Ala Thr Leu Gly Val Asp Leu Ser His Lys Ala Gly Phe
        35                  40                  45

Ile Arg Asp Gln Met Asp Leu Phe Phe Gly Pro Arg Leu Gln Pro Gln
 50                  55                  60

Pro Leu Thr Thr Pro Gln Leu Ala Pro Pro Pro Gln Ala Val Val
 65                  70                  75                  80

Ala Pro Ala Asp Ala Val Pro Gln Pro Gln Pro Gln His Gln Val Leu
                85                  90                  95

Pro Gln Ala Pro Pro Ser Ala Gln Gln Met Gln Pro Gln Gln Leu Ala
            100                 105                 110

Pro Leu Gln Pro Gln Leu Met Phe Gln Thr Ile His Gln Leu Pro Ala
        115                 120                 125

Ile Ser Pro Val Pro Val Val Ser Ala Pro Pro Ala Met Ala Phe Tyr
130                 135                 140

Pro Pro Pro Pro Leu Ala Phe Arg Tyr Thr Thr Gly Leu Ala Gly Ala
145                 150                 155                 160

Ala Thr Gly Gly Thr Val Ser Phe Gln Gln Pro Ala Pro Gly Ala Gly
                165                 170                 175

Gly Thr Ala Ser Pro Thr Ala Ala Pro Gln Val Ala Gly Asp Asn Lys
            180                 185                 190

Glu Ser Ser Ser Lys Arg Lys Arg Gly Gly Pro Gly Gly Leu Asn Lys
        195                 200                 205

Val Cys Ala Ile Ser Pro Glu Leu Gln Thr Ile Val Gly Glu Thr Ala
210                 215                 220

Met Ser Arg Thr Gln Ile Val Lys Gln Leu Trp Ala Tyr Ile Arg Gln
225                 230                 235                 240

Asn Asn Leu Gln Asp Pro Asp Asp Lys Arg Lys Ile Ile Cys Asn Asp
                245                 250                 255

Glu Leu Arg Val Val Phe Glu Thr Asp Thr Asp Met Phe Lys Met
            260                 265                 270

Asn Lys Leu Leu Ala Lys His Ile Thr Pro Leu Asp Pro Lys Ser Gln
        275                 280                 285

Leu His Glu Val Lys Arg Met Lys Ala Pro Thr Met Ser Pro Gln Pro
290                 295                 300

Gly Arg Pro Ile Asp Gln Pro Ser Ile Val Ile Ser Asp Ala Leu Ala
305                 310                 315                 320

Lys Phe Ile Gly Thr Asp Gly Thr Phe Pro Gln Asp Ala Leu Lys
                325                 330                 335

Tyr Leu Trp Asp Tyr Ile Lys Ala Asn Gln Leu Glu Asp Val Ile Asn
            340                 345                 350

Glu Ser Ile Leu Cys Asp Ser Lys Leu Gln Glu Leu Phe Gly Cys Glu
        355                 360                 365

Ser Ile Pro Met Ser Gly Leu Ser Glu Met Leu Gly His His Phe Ile
370                 375                 380

Lys Lys Thr
```

<210> SEQ ID NO 6
<211> LENGTH: 406
<212> TYPE: PRT
<213> ORGANISM: Oryza sativa (japonica cultivar-group)

<400> SEQUENCE: 6

| | | | | | | | | | | | | | | | |
|---|---|---|---|---|---|---|---|---|---|---|---|---|---|---|---|
| Met | Leu | Ser | Asp | Gln | Glu | Leu | Ala | Arg | Tyr | Val | Glu | Ser | Phe | Val | Arg |
| 1 | | | | 5 | | | | | 10 | | | | | 15 | |
| Gln | Ala | Ala | Ala | Val | Pro | Gly | Ala | Val | Ala | Ala | Gly | Gly | Ile | Ser | |
| | | | 20 | | | | | 25 | | | | | 30 | | |
| Ala | Glu | Ser | Val | Ala | Arg | Gln | Leu | Gly | Pro | Gln | Leu | Gly | Leu | Asp | Leu |
| | | | 35 | | | | | 40 | | | | | 45 | | |
| Thr | Pro | Lys | Ala | Pro | Leu | Ile | Arg | Asp | Ile | Leu | Leu | Ala | Leu | Phe | Ser |
| | | 50 | | | | | 55 | | | | | 60 | | | |
| Pro | Pro | Pro | Gln | Gly | Ala | Pro | Phe | Thr | Ser | Ser | Ala | Pro | Ser | Pro | Ser |
| 65 | | | | | 70 | | | | | 75 | | | | | 80 |
| Ala | Ser | Ala | Ser | Ala | Ser | Ala | Ser | Ala | Ala | Ala | Gly | His | Phe | Phe | |
| | | | | 85 | | | | | 90 | | | | | 95 | |
| Ser | Gln | Gln | Gln | Gln | Gln | Gln | Leu | Gln | Thr | Phe | Leu | Thr | Ala | Ser | |
| | | | | 100 | | | | | 105 | | | | | 110 | |
| Gln | Gln | Tyr | Gln | His | Arg | Gly | Ala | Gly | Ala | Ala | Ala | Ala | Pro | Pro | |
| | | | | 115 | | | | | 120 | | | | | 125 | |
| Ser | Ala | Tyr | Gly | Val | Ala | Ala | Ala | Ala | Gly | Tyr | Arg | Tyr | Gly | Gln | |
| | | | 130 | | | | | 135 | | | | | 140 | | |
| Pro | Phe | Pro | Gln | Asp | Glu | Gly | Ala | His | Leu | Gln | Arg | Leu | Val | Gln | Met |
| 145 | | | | | 150 | | | | | 155 | | | | | 160 |
| His | His | His | Gln | Gln | Gln | Gln | Gln | Gln | Gln | Gln | Gln | Gln | Gln | Met | Ala |
| | | | | 165 | | | | | 170 | | | | | 175 | |
| Ala | Ala | Ala | Ala | Gly | Val | Ala | Ala | Ala | Pro | Pro | Thr | Ala | Val | Glu | Ser |
| | | | 180 | | | | | 185 | | | | | 190 | | |
| Pro | Arg | Pro | Ala | Ala | Ala | Ser | Lys | Lys | Glu | Ser | Ala | Ser | Thr | Gly | Val |
| | | | | 195 | | | | | 200 | | | | | 205 | |
| Lys | Arg | Arg | Gly | Gly | Pro | Gly | Gly | Leu | Asn | Lys | Val | Cys | Gly | Val | Ser |
| | | 210 | | | | | 215 | | | | | 220 | | | |
| Pro | Glu | Leu | Gln | Ala | Ile | Val | Gly | Glu | Pro | Thr | Met | Ala | Arg | Thr | Glu |
| 225 | | | | | 230 | | | | | 235 | | | | | 240 |
| Ile | Val | Lys | Gln | Leu | Trp | Ala | Tyr | Ile | Arg | Arg | Asn | Asn | Leu | Gln | Asp |
| | | | | 245 | | | | | 250 | | | | | 255 | |
| Pro | Asn | Asn | Lys | Arg | Lys | Ile | Ile | Cys | Asn | Asp | Glu | Leu | Arg | Leu | Val |
| | | | 260 | | | | | 265 | | | | | 270 | | |
| Phe | Glu | Thr | Asp | Ser | Thr | Asp | Met | Phe | Lys | Met | Asn | Lys | Leu | Leu | Ala |
| | | | | 275 | | | | | 280 | | | | | 285 | |
| Lys | His | Ile | Arg | Pro | Leu | Glu | Ala | Lys | Lys | Asp | Ser | Asn | Arg | Asp | Ser |
| | | | | 290 | | | | | 295 | | | | | 300 | |
| Lys | Lys | Leu | Lys | Pro | Val | Asp | Ser | Glu | Pro | Ile | Ser | Pro | Ala | Glu | Thr |
| 305 | | | | | 310 | | | | | 315 | | | | | 320 |
| Asp | Val | Asn | Gln | Leu | Pro | Ile | Ile | Leu | Ser | Asp | Ala | Leu | Ala | Ser | Phe |
| | | | | 325 | | | | | 330 | | | | | 335 | |
| Phe | Gly | Thr | Gly | Glu | Lys | Glu | Met | Pro | Ser | Ser | Glu | Ala | Val | Lys | Arg |
| | | | 340 | | | | | 345 | | | | | 350 | | |
| Val | Trp | Asp | His | Ile | Lys | Ser | Asn | Asn | Leu | Glu | Asp | Pro | Ala | Asn | Pro |
| | | | | 355 | | | | | 360 | | | | | 365 | |

```
Thr Met Ile Leu Cys Asp Ser Lys Leu Lys Gln Leu Phe Gly Cys Glu
    370                 375                 380

Ser Leu Thr Ala Val Ser Val Ser Glu Leu Leu Ser Gln His Leu Phe
385                 390                 395                 400

Lys Gln Pro Asn Lys Leu
                405

<210> SEQ ID NO 7
<211> LENGTH: 1954
<212> TYPE: DNA
<213> ORGANISM: Arabidopsis thaliana

<400> SEQUENCE: 7
gtgggtaaaa gtatccttct ttgtgcattt ggtattttta agcatgtaat aagaaaaacc      60
aaaatagacg gctggtattt aataaaagga gactaatgta tgtatagtat atgatttgtg     120
tggaatataa taaagttgta aaatatagat gtgaagcgag tatctatctt ttgactttca     180
aaggtgatcg atcgtgttct ttgtgatagt tttggtcgtc ggtctacaag tcaacaacca     240
ccttgaagtt ttcgcgtctc ggtttcctct tcgcatctgg tatccaatag catacatata     300
ccagtgcgga aaatggcgaa gactagtggg cttgaaccat aaggtttggc cccaatacgg     360
attccaaaca acaagcctag cgcagtcttt tgggatgcat aagactaaac tgtcgcagtg     420
atagacgtaa gatatatcga cttgattgga atcgtctaag ctaataagtt taccttgacc     480
gtttatagtt gcgtcaacgt ccttatggag attgatgccc atcaaataaa cctgaaaatc     540
catcaccatg accaccataa actcccttgc tgccgctgct ttggcttgag caaggtgttt     600
ccttgtaaag ctccgatctt tggataaagt gttccacttt ttgcaagtag ctctgacccc     660
tctcagagat gtcaccggaa tcttagacag aacctcctct gccaaatcac ttggaagatc     720
ggacaatgtc atcatttttg caggtaattt ctccttcgtt gctgctttgg cttgagcacg     780
gtgcttcttt gtaaagctcc gatctttgga taagagcgga tcggaatcct ctaggaggtg     840
ccagtccctt gacctattaa tttatagaag gttttagtgt attttgttcc aatttcttct     900
ctaacttaac aaataacaac tgcctcatag tcatgggctt caaatttttat cgcttggtgt     960 atttcgttat ttgcaaggcc ttggcccatt ttgagcccaa taactaaatc tagccttttc    1020
agaccggaca tgaacttcgc atattggcgt aactgtgcag ttttaccttt ttcggatcag    1080
acaagatcag atttagacca cccaacaata gtcagtcata tttgacaacc taagctagcc    1140
gacactacta aaaagcaaac aaaagaagaa ttctatgttg tcattttacc ggtggcaagt    1200 ggaccctttct ataaaagagt aaagagacag cctgtgtgtg tataatctct aattatgttc    1260
accgacacaa tcacacaaac ccttctctaa tcacacaact tcttcatgat ttacgacatt    1320
aattatcatt aactctttaa attcacttta catgctcaaa aatatctaat ttgcagcatt    1380
aatttgagta ccgataacta ttattataat cgtcgtgatt cgcaatcttc ttcattagat    1440
gctgtcaagt tgtactcgca cgcggtggtc cagtgaagca aatccaacgg tttaaaacct    1500 tcttacatttt ctagatctaa tctgaaccgt cagatatcta gatctcattg tctgaacaca    1560
gttagatgaa actgggaatg aatctggacg aaattacgat cttacaccaa cccctcgac     1620 gagctcgtat atataaagct tatacgctcc tccttcacct tcgtactact actaccacca    1680 catttctttta gctcaaccct cattactaat ctccttttaa ggtatgttca ctttctcttg    1740
```

```
attcatactt tctcaagatt cctgcatttc tgtagaattt gaaccaagtg tcgatttttg    1800
tttgagagaa gtgttgattt atagatctgg ttattgaatc tagattccaa tttttaattg    1860
attcgagttt gttatgtgtg tttatactac ttctcattga tcttgtttga tttctctgct    1920
ctgtattagg tttctttcgt gaatcagatc ggaa                                 1954
```

<210> SEQ ID NO 8
<211> LENGTH: 2016
<212> TYPE: DNA
<213> ORGANISM: Arabidopsis thaliana

<400> SEQUENCE: 8

```
gatcggcctt cttcaggtct tctctgtagc tctgttactt ctatcacagt tatcgggtat      60
ttgagaaaaa agagttagct aaaatgaatt tctccatata atcatggttt actacaggtt     120
tacttgattc gcgttagctt tatctgcatc caaagttttt tccatgatgt tatgtcatat     180
gtgataccgt tactatgttt ataactttat acagtctggt tcactggagt ttctgtgatt     240
atgttgagta catactcatt catcctttgg taactctcaa gtttaggttg tttgaattgc     300
ctctgttgtg atacttattg tctattgcat caatcttcta atgcaccacc ctagactatt     360
tgaacaaaga gctgtttcat tcttaaacct ctgtgtctcc ttgctaaatg gtcatgcttt     420
aatgtcttca cctgtctttc tcttctatag atatgtagtc ttgctagata gttagttcta     480
cagctctctt ttgtagtctt gttagagagt tagttgagat attacctctt aaaagtatcc     540
ttgaacgctt tccggttatg accaatttgt tgtagctcct tgtaagtaga acttactggg     600
accagcgaga cagtttatgt gaatgttcat gcttaagtgt cgaacgtatc tatctctact     660
atagctctgt agtcttgtta gacagttagt tttatatctc catttttttg tagtcttgct     720
agttgagata ttacctcttc tcttcaaagt atccttgaac gctcaccggt tatgaaatct     780
ctacactata gctctgtagt cttgctagat agttagttct ttagctctct ttttgtagcc     840 tagttctttta gctctccttt tgtagccttg ctacagagta agatgggata ttacctcctt     900
gaacgctctc cggttatgac caatttgttg tagctccttg taagtagaac ttaggataga     960
gtgagtcaac tttaagaaag aacctagtat gtggcataac cagattgcag gctctgtctc    1020
ggctacagta acgtaactct atagctcttt gttttgttca gaaagaacca gtgattggat    1080
gattcgtcct tagaaactgg acctaacaac agtcattggc tttgaaatca agccacaaca    1140
atgcctatat gaaccgtcca tttcatttat ccgtttcaaa ccagcccatt acatttcgtc    1200
ccattgataa ccaaaagcgg ttcaatcaga ttatgtttta attttaccaa attctttatg    1260
aagtttaaat tatactcaca ttaaaaggat tattggataa tgtaaaaatt ctgaacaatt    1320
actgattttg gaaaattaac aaatattctt tgaaatagaa gaaaaagcct ttttcctttt    1380
gacaacaaca tataaaatca tactcccatt aaaaagattt taatgtaaaa ttctgaatat    1440
aagatatttt ttacaacaac aaccaaaaat atttattttt ttccttttttt acagcaacaa    1500 gaaggaaaaa cttttttttt tgtcaagaaa aggggagatt atgtaaacag ataaaacagg    1560
gaaaataact aaccgaactc tcttaattaa catcttcaaa taaggaaaat tatgatccgc    1620
atatttagga agatcaatgc attaaaacaa cttgcacgtg aaagagaga ctatacgctc     1680 cacacaagtt gcactaatgg tacctctcac aaaccaatca aaatactgaa taatgccaac    1740
```

-continued

```
gtgtacaaat tagggtttta cctcacaacc atcgaacatt ctcgaaacat tttaaacagc    1800
ctggcgccat agatctaaac tctcatcgac caatttttga ccgtccgatg gaaactctag    1860
cctcaaccca aaactctata taaagaaatc ttttccttcg ttattgctta ccaaatacaa    1920
accctagccg ccttattcgt cttcttcgtt ctctagtttt ttcctcagtc tctgttctta    1980
gatcccttgt agtttccaaa tcttccgata aggcct                              2016
```